(12) United States Patent  (10) Patent No.: US 9,332,964 B2
Miyake  (45) Date of Patent: *May 10, 2016

(54) ULTRASOUND OBSERVATION SYSTEM

(71) Applicant: OLYMPUS MEDICAL SYSTEMS CORP., Tokyo (JP)

(72) Inventor: Tatsuya Miyake, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 15 days.

This patent is subject to a terminal disclaimer.

(21) Appl. No.: 14/339,006

(22) Filed: Jul. 23, 2014

(65) Prior Publication Data

US 2015/0018680 A1 Jan. 15, 2015

Related U.S. Application Data

(63) Continuation of application No. PCT/JP2013/078075, filed on Oct. 16, 2013.

(30) Foreign Application Priority Data

Jan. 18, 2013 (JP) ................................. 2013-007609

(51) Int. Cl.
*A61B 8/00* (2006.01)
*A61B 8/08* (2006.01)
*A61B 8/12* (2006.01)

(52) U.S. Cl.
CPC ................. *A61B 8/485* (2013.01); *A61B 8/085* (2013.01); *A61B 8/12* (2013.01); *A61B 8/5207* (2013.01); *A61B 8/54* (2013.01); *A61B 8/429* (2013.01); *A61B 8/543* (2013.01)

(58) Field of Classification Search
CPC ...... A61B 8/145; A61B 8/483; A61B 5/0048; A61B 5/0064; A61B 5/1127; A61B 8/08; A61B 8/485; A61B 2562/043; G01S 7/2033; G01S 15/8934; G01S 15/8979; G01S 15/8993
See application file for complete search history.

(56) References Cited

U.S. PATENT DOCUMENTS

| 7,435,232 B2* | 10/2008 | Liebschner .......... A61B 5/0048 128/920 |
| 2004/0236223 A1 | 11/2004 | Barnes et al. |
| 2008/0249408 A1* | 10/2008 | Palmeri .................... A61B 8/08 600/438 |
| 2011/0301468 A1 | 12/2011 | Sandrin et al. |
| 2015/0126866 A1* | 5/2015 | Miyake ................ A61B 5/0402 600/438 |

FOREIGN PATENT DOCUMENTS

| DE | 199 33 882 A1 | 1/2001 |
| EP | 1 637 081 A1 | 3/2006 |

(Continued)

OTHER PUBLICATIONS

Extended Supplementary European Search Report dated Nov. 18, 2015 issued in European Application No. 13 87 2193.1.

*Primary Examiner* — Joel Lamprecht

(74) *Attorney, Agent, or Firm* — Scully, Scott, Murphy & Presser, PC

(57) ABSTRACT

An ultrasound observation system includes an ultrasound transducer that generates an ultrasound signal by transmitting and receiving ultrasound to and from a subject, an automatic pressurizing mechanism that applies a pressing force to the subject to cause pressurizing displacement, an elastic-image-generation displacement measuring circuit that measures an imaging displacement amount of the subject based on the ultrasound signal, an elastic modulus calculation circuit that calculates an elastic modulus of the subject based on the imaging displacement amount, a pressurizing-mechanism-control displacement measuring circuit that measures a controlling displacement amount in accordance with spontaneous displacement of the subject based on the ultrasound signal, and a pressurizing mechanism control circuit that controls the automatic pressurizing mechanism based on the controlling displacement amount.

16 Claims, 6 Drawing Sheets

(56) References Cited

FOREIGN PATENT DOCUMENTS

| | | |
|---|---|---|
| EP | 2 263 545 A1 | 12/2010 |
| JP | 2004-351062 A | 12/2004 |
| JP | 2007-082725 A | 4/2007 |
| JP | 2007-301086 A | 11/2007 |
| JP | 2008-183097 A | 8/2008 |
| JP | 2011-189042 A | 9/2011 |
| JP | 2012-249776 A | 12/2012 |
| WO | WO 2006/041050 A1 | 4/2006 |
| WO | WO 2011/034005 A1 | 3/2011 |

* cited by examiner

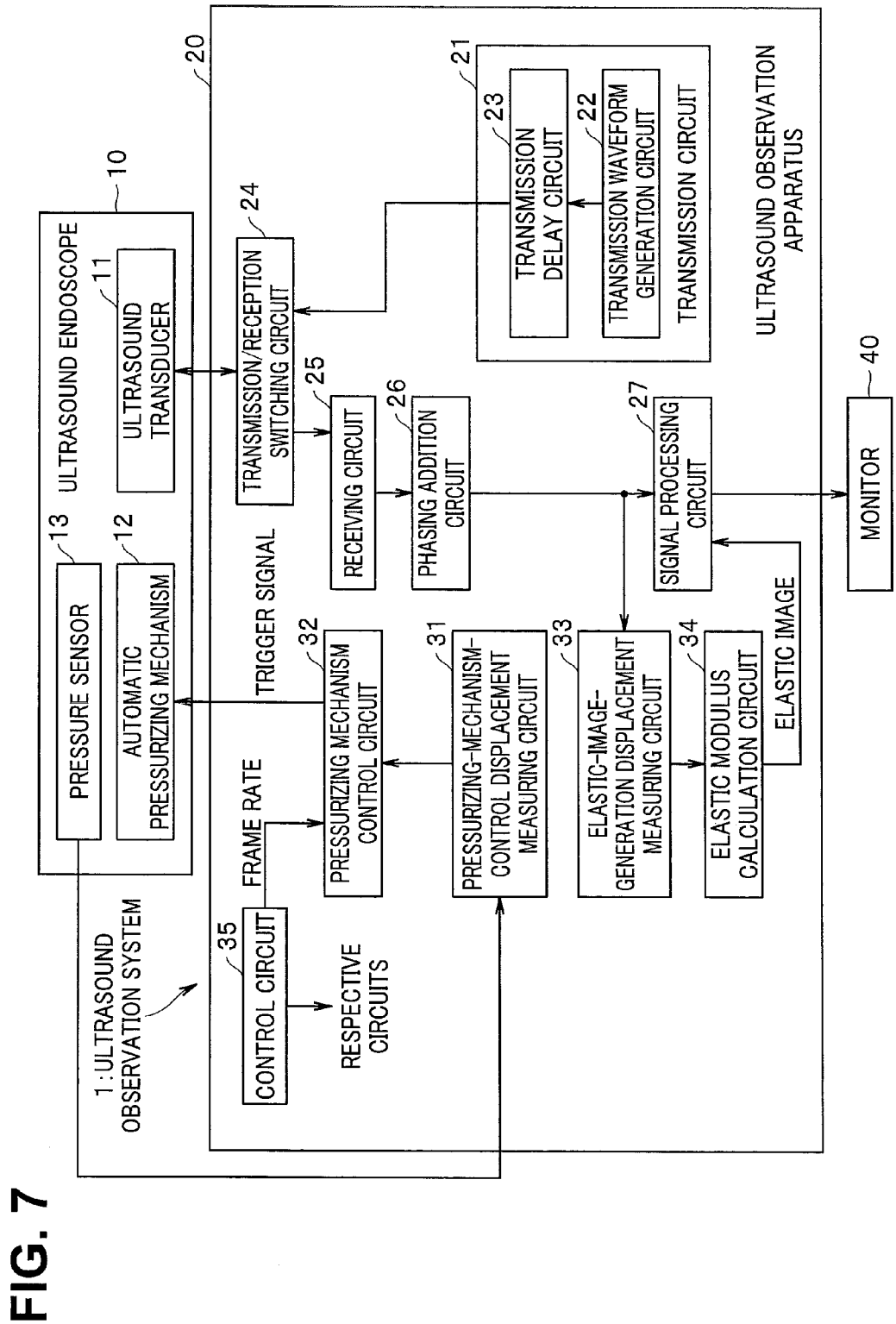

ULTRASOUND OBSERVATION SYSTEM

CROSS REFERENCE TO RELATED APPLICATION

This application is a continuation application of PCT/JP2013/078075 filed on Oct. 16, 2013 and claims benefit of Japanese Application No. 2013-007609 filed in Japan on Jan. 18, 2013, the entire contents of which are incorporated herein by this reference.

BACKGROUND OF THE INVENTION

1. Field of the Invention

The present invention relates to an ultrasound observation system that generates an image including an elastic image based on an ultrasound signal obtained by transmitting and receiving ultrasound.

2. Description of the Related Art

An ultrasound diagnostic apparatus that generates an elastic image indicative of hardness or softness of a living tissue from a distortion amount of the living tissue caused by an oppression force has been put into practical use.

For example, in Japanese Patent Laid-Open Publication No. 2004-351062, there is described an ultrasound diagnostic apparatus in which external forces are applied to a subject by a surgeon using a probe and a plurality of tomographic image data which are different in time are acquired, and not only displacement of respective tissues but also modulus of elasticity are calculated based on the acquired tomographic image data, to create an elastic image. Further, there is described a technique of measuring a pressure in order to obtain an appropriate elastic image and displaying an appropriate pressure range.

Further, in International Patent Publication WO2006/041050, there is described an extracorporeal ultrasound probe capable of performing elasticity measurement which is configured to be able to perform automatic pressurization so as to obtain an appropriate elastic data. Further, it is described that an oppressing speed of an oppressing action is controlled in the automatic pressurization based on period information of an ultrasound reception signal frame data.

Incidentally, in a case where the subject is a living body or the like, there is a case where a pressure action having a certain rhythm due to spontaneous displacement of the subject such as a pulse beat or a pulsation is found. Therefore, it is conceivable to obtain an elastic image based on such spontaneous displacement of the subject.

SUMMARY OF THE INVENTION

An ultrasound observation system according to an aspect of the present invention transmits ultrasound to a subject, receives the ultrasound reflected by the subject and generates an image based on an ultrasound signal obtained by the received ultrasound, and the ultrasound observation system includes: an ultrasound transducer that transmits the ultrasound to the subject, receives the ultrasound reflected by the subject and generates the ultrasound signal from the received ultrasound; a pressurizing section that applies a pressing force to the subject to cause pressurizing displacement; a displacement-related-amount detecting section that detects a displacement related amount relating to displacement of the subject; an elastic-image displacement measuring section that measures an imaging displacement amount of the subject based on the ultrasound signal so as to generate an elastic image of the subject; an elastic modulus calculation section that calculates an elastic modulus of the subject based on the imaging displacement amount; a pressurizing-control displacement measuring section that measures a controlling displacement amount in accordance with spontaneous displacement of the subject based on the displacement related amount so as to control the pressurizing section; and a pressurizing control section that controls the pressurizing section based on the controlling displacement amount.

BRIEF DESCRIPTION OF THE DRAWINGS

FIG. 7 is a block diagram showing a configuration of an ultrasound observation system in embodiment 2 of the present invention.

DETAILED DESCRIPTION OF THE PREFERRED EMBODIMENTS

Figure 1:
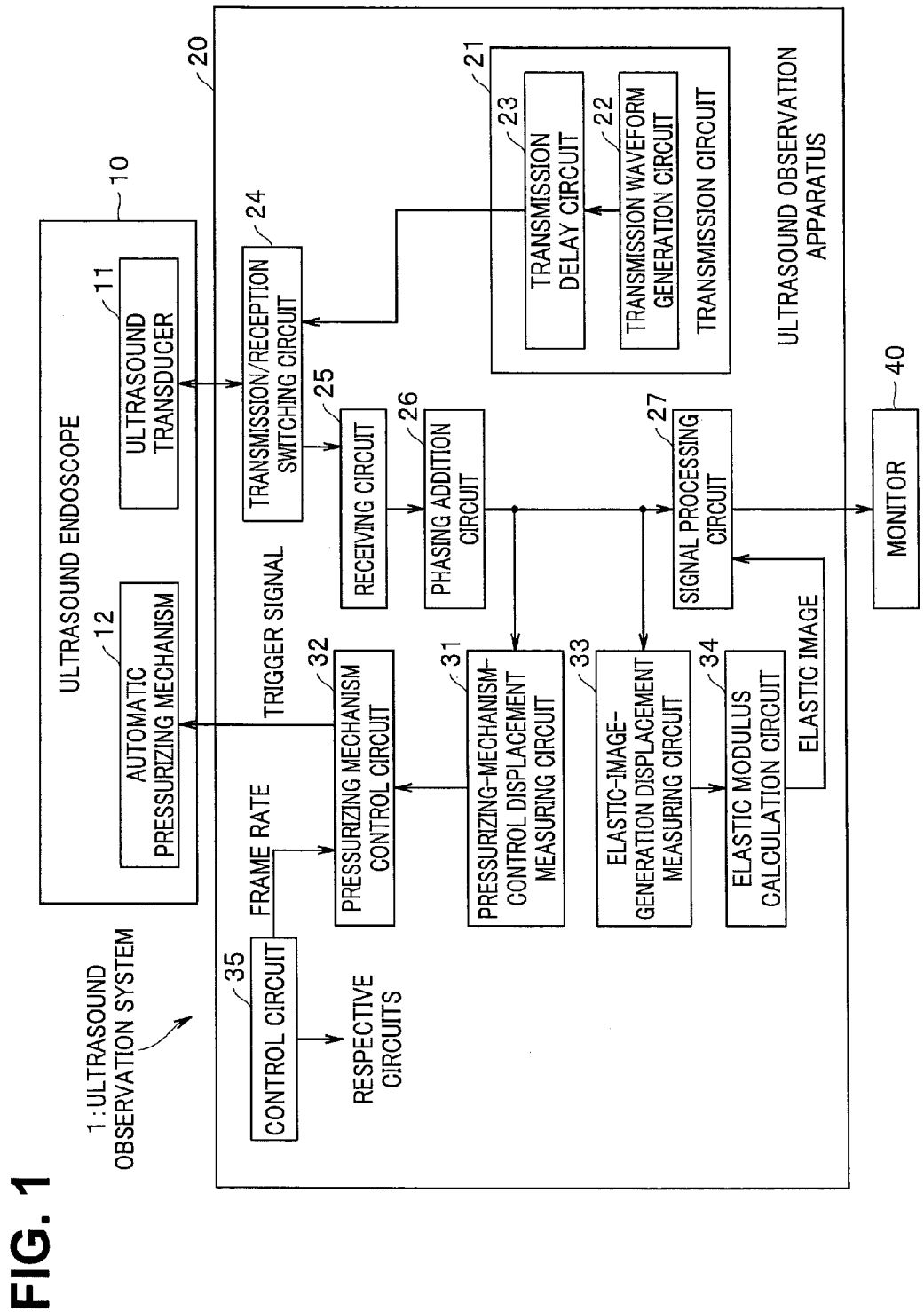
FIG. 1 is a block diagram showing a configuration of an ultrasound observation system in embodiment 1 of the present invention.

Hereinafter, embodiments of the present invention will be described referring to the drawings.

Embodiment 1

FIG. 1 through FIG. 6 show embodiment 1 of the present invention and FIG. 1 is a block diagram showing a configuration of an ultrasound observation system 1.

The ultrasound observation system 1 is a system that transmits ultrasound to a subject and receives ultrasound reflected by the subject, and generates an image based on an ultrasound signal obtained from the received ultrasound, and comprises an ultrasound endoscope 10, an ultrasound observation apparatus 20 and a monitor 40.

The ultrasound endoscope 10 is a probe comprising an ultrasound transducer 11 and an automatic pressurizing mechanism 12.

The ultrasound transducer 11 transmits ultrasound to the subject and receives ultrasound reflected by the subject and generates an ultrasound signal from the received ultrasound, and is configured for example as a transducer array in which a number of transducer elements are arranged.

The automatic pressurizing mechanism 12 is a pressurizing section which applies a pressing force to the subject to case pressurizing displacement at timing on the basis of a trigger signal from a pressurizing mechanism control circuit 32, as described later. The automatic pressurizing mechanism 12 may be configured such that, for example, a pressurizing surface which comes into contact with the subject is vibrated using a driving source such as a motor, or such that a fluid (which is preferably a liquid in consideration that the ultrasound transmitted and received by the ultrasound transducer 11 is not attenuated) is caused to enter and exit a balloon and a balloon surface, which is a pressurizing surface which comes into contact with the subject, is vibrated, or other configurations may be adopted.

The ultrasound observation apparatus 20 comprises a transmission circuit 21, a transmission/reception switching circuit 24, a receiving circuit 25, a phasing addition circuit 26, a signal processing circuit 27, a pressurizing-mechanism-control displacement measuring circuit 31, the pressurizing mechanism control circuit 32, an elastic-image-generation displacement measuring circuit 33, an elastic modulus calculation circuit 34, and a control circuit 35.

The transmission circuit 21 includes a transmission waveform generation circuit 22 and a transmission delay circuit 23.

The transmission waveform generation circuit 22 generates and outputs a signal waveform for driving the respective transducer elements constituting the ultrasound transducer 11.

The transmission delay circuit 23 adjusts drive timing of the respective transducer elements constituting the ultrasound transducer 11. Thereby, a focus and a direction of an ultrasound beam transmitted from the ultrasound transducer 11 are controlled and the ultrasound can be converged at a desired position (depth).

The transmission/reception switching circuit 24 includes, for example, a multiplexer which sequentially selects the plurality of transducer elements for performing transmission and reception of the ultrasound, transmits a drive signal from the transmission circuit 21 to the ultrasound transducer 11, and transmits the ultrasound signal (echo signal) from the ultrasound transducer 11 to the receiving circuit 25.

The receiving circuit 25 receives the ultrasound signal from the transmission/reception switching circuit 24 and performs processing of amplification, conversion into a digital signal, etc.

The phasing addition circuit 26 performs addition of the ultrasound signals after phase matching by delaying the ultrasound signals.

In an ultrasound diagnosis mode, the signal processing circuit 27 performs coordinate transformation and interpolation processing of the ultrasound signal from the phasing addition circuit 26 and creates an ultrasound image as an image for display. Further, in an elastic image observation mode, the signal processing circuit 27 creates an elastic image from the elastic modulus calculation circuit 34 as an image for display, or creates an image for display by superimposing the elastic image on the ultrasound image.

The pressurizing-mechanism-control displacement measuring circuit 31 is a pressurizing-mechanism-control displacement measuring section that measures a controlling displacement amount of the subject (a displacement amount for controlling the automatic pressurizing mechanism 12 which is the pressurizing section) based on the ultrasound signal from the phasing addition circuit 26. Therefore, in the present embodiment, the ultrasound transducer 11 serves as a displacement-related-amount detecting section that detects a displacement related amount which relates to displacement of the subject, and the displacement related amount is the ultrasound signal generated by the ultrasound transducer 11.

The pressurizing mechanism control circuit 32 is a pressurizing control section that controls the automatic pressurizing mechanism 12 by generating the trigger signal based on the controlling displacement amount measured by the pressurizing-mechanism-control displacement measuring circuit 31 and by outputting the generated signal to the automatic pressurizing mechanism 12. The pressurizing mechanism control circuit 32 calculates a period at which the controlling displacement amount on the basis of spontaneous displacement of the subject is equal to or greater than a preset threshold, and controls the automatic pressurizing mechanism 12 to apply the pressing force with timing according to the calculated period.

The elastic-image-generation displacement measuring circuit 33 is an elastic-image displacement measuring section that measures an imaging displacement amount of the subject (a displacement amount for generating an elastic image of the subject) based on the ultrasound signal.

It is noted that, in the present embodiment, since the displacement-related-amount detecting section is constituted by the ultrasound transducer 11 as described above, both of the pressurizing-mechanism-control displacement measuring circuit 31 and the elastic-image-generation displacement measuring circuit 33 detect the displacement amount based on the ultrasound signal. Therefore, in the following, the description will be given assuming that configurations of basic displacement amount detection portions in the pressurizing-mechanism-control displacement measuring circuit 31 and the elastic-image-generation displacement measuring circuit 33 are made common (referred to as a common displacement measuring circuit, etc.).

The elastic modulus calculation circuit 34 is an elastic modulus calculation section that calculates an elastic modulus of the subject based on the imaging displacement amount measured by the elastic-image-generation displacement measuring circuit 33. The elastic modulus calculation circuit 34 calculates the elastic modulus at respective coordinates of the subject and therefore the calculation result becomes an elastic image in which the elastic moduli are distributed on two-dimensional coordinates.

The control circuit 35 controls the respective circuits in the ultrasound observation apparatus 20 and outputs information of a frame rate to the pressurizing mechanism control circuit 32.

The monitor 40 displays the image for display from the signal processing circuit 27.

Figure 2:
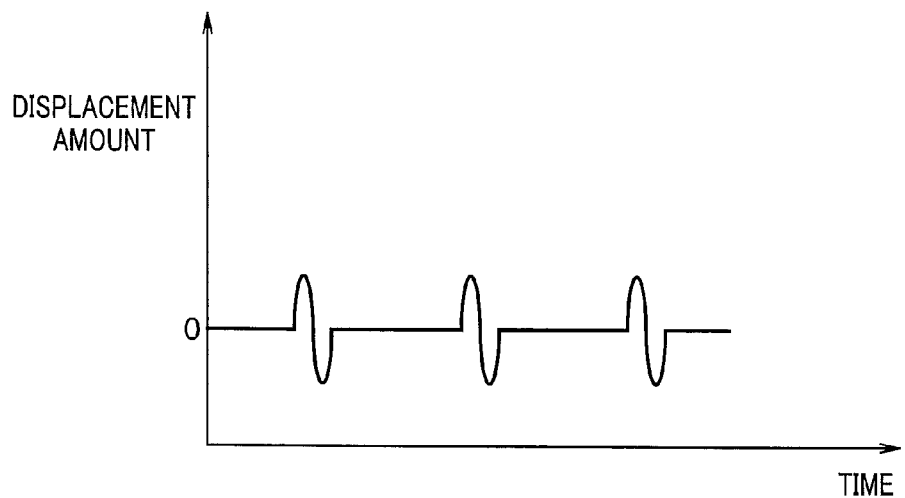
FIG. 2 is a diagram showing an example of spontaneous displacement of a subject measured by a pressurizing-mechanism-control displacement measuring circuit when a pressing force is not applied by an automatic pressurizing mechanism.

FIG. 2 is a diagram showing an example of the spontaneous displacement of the subject measured by the pressurizing-mechanism-control displacement measuring circuit 31 when the pressing force is not applied by the automatic pressurizing mechanism 12.

When the spontaneous displacement of the subject is a pulse beat or a pulsation, for example, positive and negative amplitudes are generated with respect to a vibration center at certain time intervals to be periodical displacements as shown in the figure.

Figure 3:
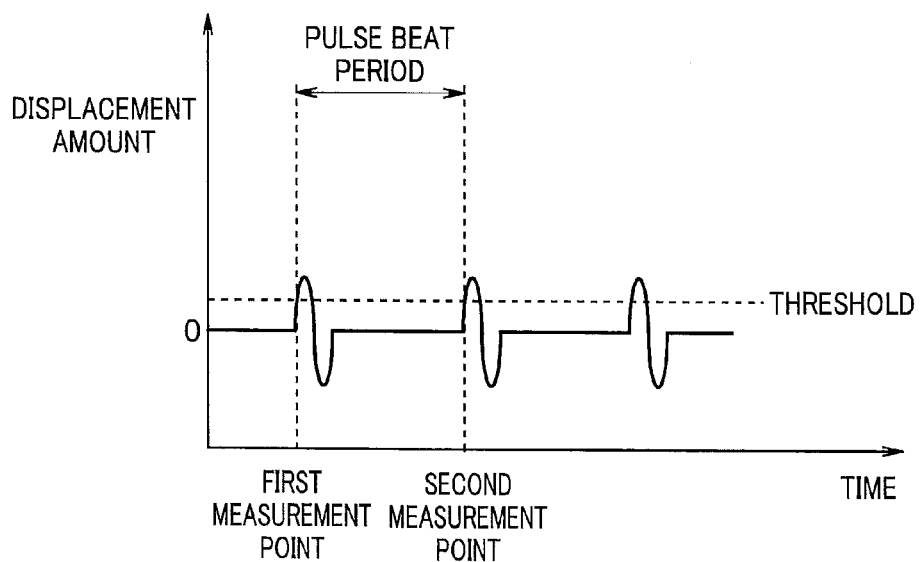
FIG. 3 is a diagram for explaining a method of calculating a period of the spontaneous displacement of the subject in the above embodiment 1.
Figure 4:
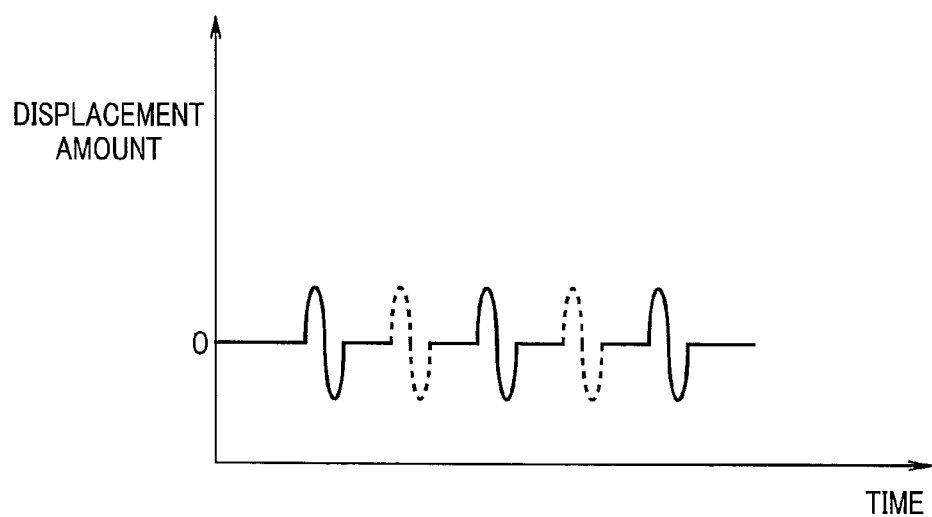
FIG. 4 is a diagram showing an example of the spontaneous displacement and pressurizing displacement of the subject measured by the pressurizing-mechanism-control displacement measuring circuit when the pressing force is applied by the automatic pressuring mechanism in the above embodiment 1.

FIG. 3 is a diagram for explaining a method of calculating the period of the spontaneous displacement of the subject, and FIG. 4 is a diagram showing an example of the spontaneous displacement and the pressurizing displacement of the subject measured by the pressurizing-mechanism-control displacement measuring circuit 31 when the pressing force is applied by the automatic pressuring mechanism 12.

In the case as shown in FIG. 2, the period of the spontaneous displacement of the subject may be simply calculated based on the measured control displacement amount, but in the case as shown in FIG. 4, it is necessary to exclude a pressurizing displacement component (shown by dotted lines) included in the controlling displacement amount.

Therefore, the pressurizing mechanism control circuit 32 calculates timing at which the automatic pressuring mechanism 12 applies the pressing force based on the timing information of the trigger signal outputted to the automatic pressuring mechanism 12, and consequently estimates at which timing the controlling displacement amount on the basis of the pressurizing displacement is generated. The controlling displacement amount on the basis of the pressurizing displacement thus estimated is a displacement amount shown by the dotted lines in FIG. 4. Further, the pressurizing mechanism control circuit 32 calculates the period based on the spontaneous displacement by calculating the period using the control displacement amount based on the spontaneous displacement shown in FIG. 2 with the estimated controlling displacement amount (the controlling displacement amount on the basis of the pressurizing displacement) excluded.

At this time, the pressurizing mechanism control circuit 32 is configured to perform stable period measurement by measuring the period on the basis of the spontaneous displacement at timing such that the control displacement amount exceeds a threshold (timing at which the control displacement amount transits from a state of being less than the threshold to a state of being not less than the threshold).

Further, the pressurizing mechanism control circuit 32 generates the trigger signal so that, when measuring the control displacement amount on the basis of the pressurizing displacement by the pressurizing-mechanism-control displacement measuring circuit 31, the timing at which the measured displacement amount exceeds the above-mentioned threshold is an equally divided point of the period, for example, and outputs the trigger signal to the automatic pressurizing mechanism 12.

The pressurizing mechanism control circuit 32 further controls the number of trigger signals to be generated within one period, and sets the number of trigger signals to be generated within one period based on the frame rate of the elastic image (i.e. the frame rate of the display image which the signal processing circuit 27 generates and also the frame rate of the ultrasound image generated according to the drive signal from the transmission circuit 21).

Further, the pressurizing mechanism control circuit 32 calculates a maximum value of the controlling displacement amount on the basis of the spontaneous displacement, and controls the automatic pressurizing mechanism 12 so that a value equivalent to the calculated maximum value is obtained as a maximum value of the controlling displacement amount on the basis of the pressurizing displacement. The maximum value of the pressurizing displacement shown in FIG. 4 is at a level equivalent to a maximum value of the spontaneous displacement. Besides, at this time, it is preferable to further configure such that elastic energy of the subject when the spontaneous displacement occurs and elastic energy of the subject when the pressurizing displacement is caused are equivalent. In this case, an area of a mountain (or a valley) of the spontaneous displacement and an area of a mountain (or a valley) of the pressurizing displacement are equivalent.

Figure 5:
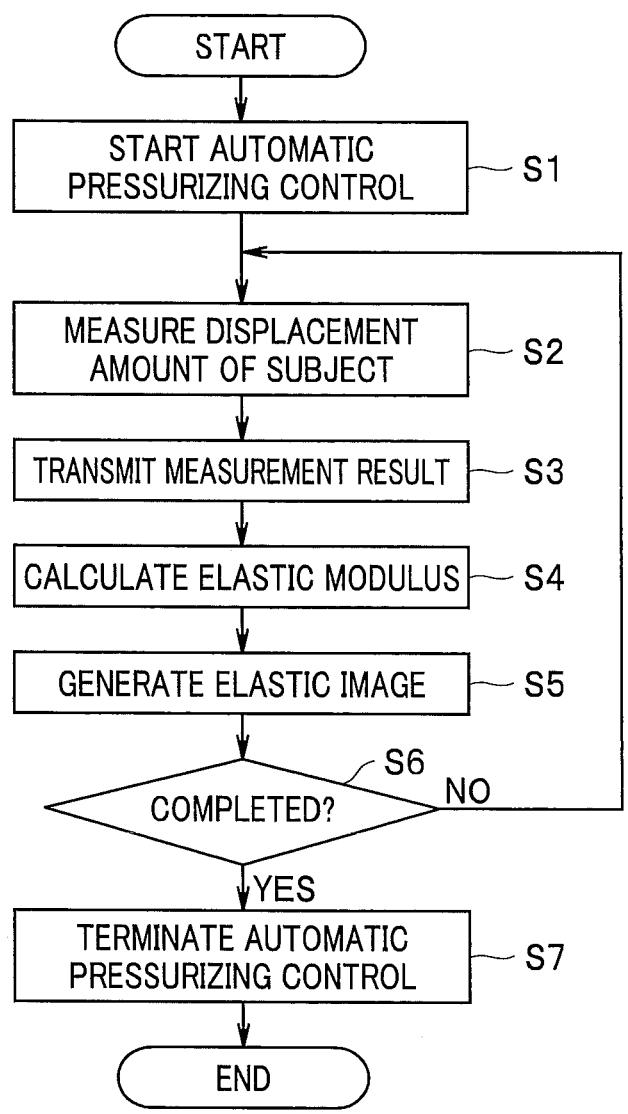
FIG. 5 is a flowchart showing elastic image generation processing in the above embodiment 1.

An operation of generating the elastic image in the ultrasound observation system 1 will be described referring to FIG. 5 and FIG. 6. FIG. 5 is a flowchart showing elastic image generation processing and FIG. 6 is a flowchart showing processing of automatic pressurizing control.

When the ultrasound observation system 1 is set to the elastic image observation mode, the processing shown in FIG. 5 is started.

Figure 6:
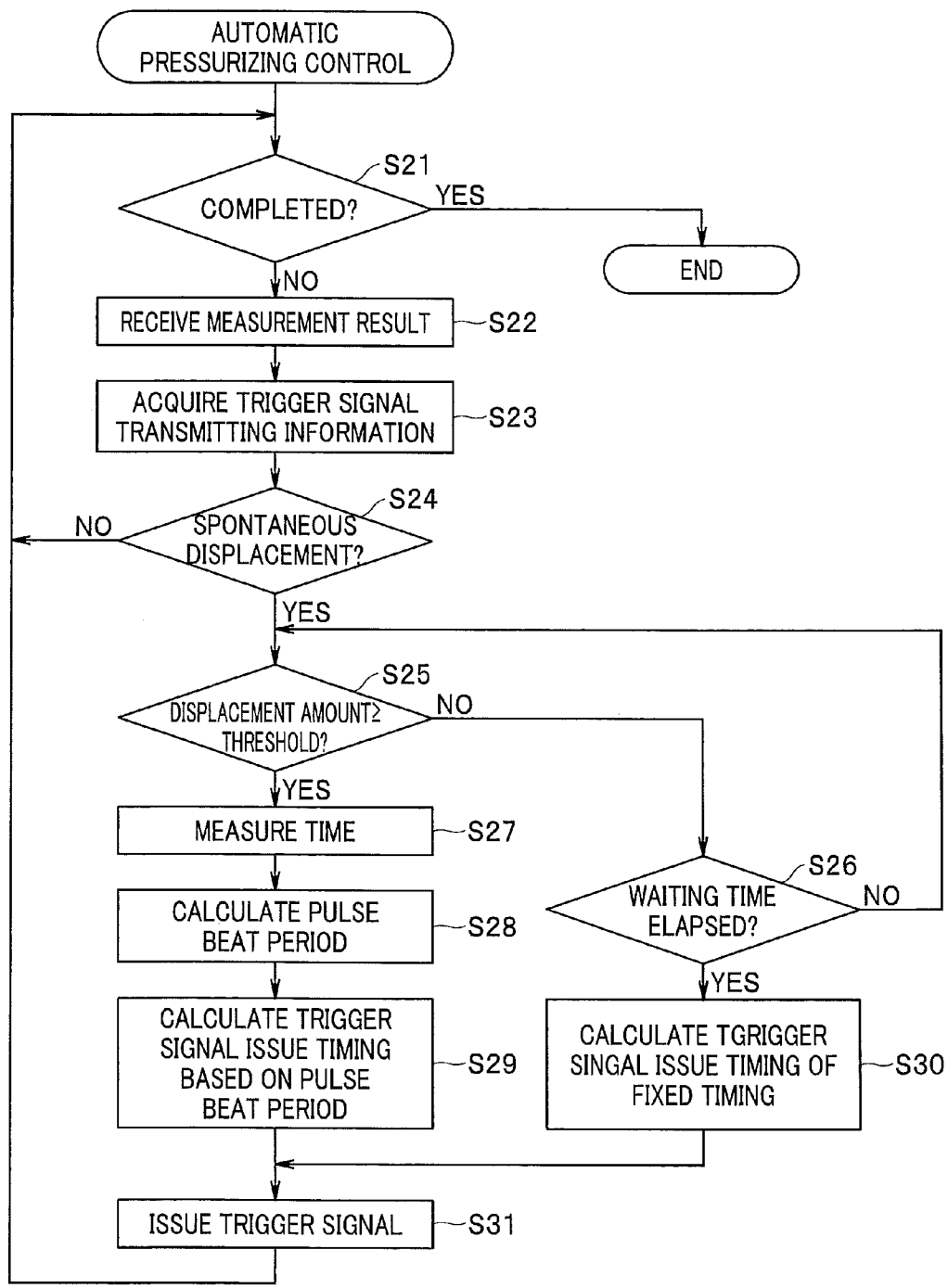
FIG. 6 is a flowchart showing processing of automatic pressurizing control in the above embodiment 1.

First, the automatic pressurizing control processing shown in FIG. 6 is started (Step S1).

Then, the displacement amount of the subject which is an object of diagnosis is measured by the common displacement measuring circuit (the common circuit part of the pressurizing-mechanism-control displacement measuring circuit 31 and the elastic-image-generation displacement measuring circuit 33) (Step S2).

Next, a result of the measurement in Step S2 is transmitted to the automatic pressurizing control processing of FIG. 6 (Step S3).

Subsequently, the elastic modulus calculation circuit 34 calculates the elastic modulus for respective coordinates of the subject based on the displacement amount (the imaging displacement amount) measured in Step S2 (Step S4).

The calculated elastic modulus is transmitted to the signal processing circuit 27 with the coordinates, in which the elastic image for display is configured (Step S5). Further, the elastic image is superimposed on the ultrasound image, as necessary, to thereby create the image for display.

Thereafter, it is determined whether or not the processing is to be terminated (Step S6) and if not completed the procedure proceeds to Step S2 and the processing as described above is repeatedly performed.

On the other hand, if it is determined that the processing is to be terminated the automatic pressurizing control processing of FIG. 6 is terminated (Step S7) and then the elastic image generation processing is terminated.

Next, the processing of automatic pressurizing control will be described.

When the automatic pressurizing control processing is started in the above-mentioned Step S1, it is determined first whether or not the automatic pressurizing control processing is to be terminated (Step S21).

The processing is still not completed, the measurement result transmitted in the above-mentioned Step S3 is received (Step S22).

Then, the pressurizing mechanism control circuit 32 acquires timing of the trigger signal transmitted to the automatic pressurizing mechanism 12, and estimates whether the controlling displacement amount received as the measurement result is on the basis of the pressurizing displacement or the spontaneous displacement (Step S23).

Further, it is determined whether or not the measurement result is on the basis of the spontaneous displacement based on the estimation (Step S24).

Here, if it is determined that the measurement result is not on the basis of the spontaneous displacement, the procedure returns to the above-mentioned Step S21.

If it is determined to be on the basis of the spontaneous displacement, the pressurizing mechanism control circuit 32 waits the timing at which the control displacement amount of the measurement result exceeds the threshold shown in FIG. 3 (the timing of transition from a state of being less than the threshold to a state of being not less than the threshold) (Step S25).

In this Step 25, if the control displacement amount has not exceeded the threshold, it is determined whether or not a time period of waiting for the timing at which the threshold is exceeded reaches a waiting time which is a predetermined time period (Step S26). Here, the waiting time is an upper-limit time period which is assumable as a period of the spontaneous displacement of the subject, and as a specific example is an upper-limit time period (e.g. two seconds) which is assumable as a period of a pulse beat of a living body.

Here, if the waiting time has not elapsed, the procedure returns to Step S25 to wait for the timing at which the threshold is exceeded.

In this way, if it is determined that the controlling displacement amount exceeds the threshold in Step S25, the time at which the control displacement amount exceeds the threshold is measured (Step S27).

Then, the period of the spontaneous displacement (e.g. the period of the pulse beat) is calculated based on the measured time (Step S28). Here, in the above-mentioned Step S25, if the controlling displacement amount exceeds the threshold for the first time from the start of the processing of automatic pressurizing control, it is a stage at which a first measurement point shown in FIG. 3 is measured and therefore the period of the spontaneous displacement cannot be calculated and the procedure proceeds to the subsequent processing without performing anything at this stage. Further, if the control displacement amount exceeds the threshold for the second time, a second measurement point shown in FIG. 3 is measured also and therefore the period of spontaneous displacement is calculated. It is noted that if the control displacement amount exceeds the threshold for the third time or subsequent times, the measurement point at which the control displacement amount exceeds the threshold latest is set to be the second measurement point and the measurement point immediately preceding this second measurement point is set to be the first measurement point, successively.

Subsequently, the pressurizing mechanism control circuit 32 calculates the timing for issuing the trigger signal based on the calculated period of the spontaneous displacement (Step S29). The calculation of the issue timing of the trigger signal is performed so that the pressurizing displacement is obtained at the equally divided point of the period of the spontaneous displacement, for example, as described above. Here, if it is intended to obtain an appropriate elastic image, it is necessary that a vibration period of the displacement amount of the subject with the spontaneous displacement and the pressurizing displacement combined is appropriate. Further, the appropriate vibration period depends on the frame rate of the elastic image. Thus, an equal division number for obtaining the appropriate vibration period is determined by the pressurizing mechanism control circuit 32 taking the frame rate of the elastic image into account (i.e. the number of trigger signals generated within one period is controlled by the pressurizing mechanism control circuit 32).

On the other hand, in Step S26, it is determined that the displacement amount does not exceed the threshold after the waiting time elapses (i.e. if the time period in which the control displacement amount on the basis of the spontaneous displacement is less than the threshold is equal to or longer than the predetermined time period), the spontaneous displacement is small and would not be appropriate for creating the elastic image in dependence on the spontaneous displacement.

Therefore, the pressurizing mechanism control circuit 32 calculates issue timing of the trigger signal which is fixed timing irrespective of the spontaneous displacement (Step S30). That is, the pressurizing mechanism control circuit 32 controls the automatic pressurizing mechanism 12 to apply the pressing force to the subject at a fixed period which is irrespective of the spontaneous displacement to thereby generate the pressurizing displacement. At this time, the pressurizing mechanism control circuit 32 sets the fixed period so as to obtain the appropriate elastic image based on the frame rate of the elastic image in the same manner as that in Step S29.

Then, the pressurizing mechanism control circuit 32 issues the trigger signal to the automatic pressurizing mechanism 12 at the timing calculated in Step S29 or Step S30 (Step S31) and the procedure returns to the processing of Step S21.

In this way, in Step S21, if a termination signal is received from the processing of the above-mentioned Step S7, the automatic pressurizing control processing is terminated.

According to the above embodiment 1, since it is configured to calculate a period at which the control displacement amount on the basis of the spontaneous displacement of the subject is equal to or greater than the threshold and to apply the pressing force to the subject at the timing in accordance with the calculated period, the appropriate elastic image can be obtained stably.

At this time, since it is configured that the control displacement amount on the basis of the pressurizing displacement is estimated by the timing at which the pressing force is applied and the period is calculated by excluding the estimated controlling displacement amount, the period on the basis of the spontaneous displacement can be calculated precisely.

Further, since the automatic pressurizing mechanism 12 applies the pressing force to the subject at timing on the basis of the inputted trigger timing, the timing of the pressurizing displacement can be controlled precisely.

Furthermore, by measuring the period on the basis of the spontaneous displacement at the timing when the control displacement amount exceeds the threshold, stable period measurement is made possible.

Moreover, since the trigger signal is generated such that the timing when the measured pressurizing displacement amount exceeds the threshold occurs at an equally divided point of the period and the generated signal is outputted to the automatic pressurizing mechanism 12, subject displacement at equally divided time intervals is obtained taking account of time lag between transmission of the trigger signal and occurrence of the displacement of the subject, to make it possible to obtain the more preferable elastic image.

In addition, since the number of trigger signals to be generated within one period can be controlled, the displacement of the subject can be generated at the most preferable period. By setting the number of trigger signals based on the frame rate of the elastic image, an elastic image in which an elastic state of the subject is easily observed can be obtained.

On the other hand, since it is configured that in a case where the spontaneous displacement is small, the pressing force at the fixed period irrespective of the spontaneous displacement is applied to the subject, an appropriate elastic image can be acquired also in this case. Here, since whether the spontaneous displacement amount is small or not is determined within the upper-limit time period which is assumable as the period of the pulse beat of the living body, the system can be entered into a state where the appropriate elastic image is acquired in a short time (without waiting for a long time in vain). By setting the fixed period at which the pressing force is applied to the subject based on the frame rate of the elastic image, the elastic image in which the elastic state of the subject is easily observed can be obtained.

Further, since it is configured that the maximum value of the pressurizing displacement amount is equivalent to the maximum value of the spontaneous displacement amount, a difference between the pressurizing displacement amount and the spontaneous displacement amount is made small and a stable elastic image can be obtained.

Furthermore, since it is configured that the ultrasound transducer 11 serves as the displacement-related-amount detecting section, it is not necessary to separately provide a displacement-related-amount detecting section in the ultrasound endoscope 10, and the configuration can be simplified. Furthermore, the receiving circuit 25 and the phasing addition circuit 26 for processing the ultrasound signal can be used also for the ultrasound image, the configuration is further simplified reasonably. In addition, since it is possible to make circuit parts of the pressurizing-mechanism-control displacement measuring circuit 31 and the elastic-image-generation displacement measuring circuit 33 common, the more concise configuration can be achieved.

Moreover, since it is configured that the ultrasound transducer 11 and the automatic pressurizing mechanism 12 are provided in the ultrasound endoscope 10 and the other circuits as described above are provided in the ultrasound observation apparatus 20, increase in size of the ultrasound endoscope 10 is suppressed as much as possible.

Embodiment 2

FIG. 7 shows embodiment 2 of the present invention and is a block diagram showing a configuration of the ultrasound observation system 1.

In this embodiment 2, the description is appropriately omitted by assigning the same reference sign to the same part as the foregoing embodiment 1 and different points will be described mainly.

In the foregoing embodiment 1, the ultrasound transducer 11 serves as the displacement-related-amount detecting section that detects the displacement related amount relating to the displacement of the subject, and the displacement related amount is the ultrasound signal generated by the ultrasound transducer 11. By contrast, the present embodiment is configured such that the displacement-related-amount detecting section is provided separately from the ultrasound transducer 11.

The ultrasound endoscope 10 comprises the ultrasound transducer 11 and the automatic pressurizing mechanism 12, and further comprises a pressure sensor 13 as the displacement-related-amount detecting section. The pressure sensor 13 is disposed, for example, at a location where the sensor is contactable with the subject at a distal end side of the ultrasound transducer 11.

It is configured that pressure detected by the pressure sensor 13 is inputted to the pressurizing-mechanism-control displacement measuring circuit 31 as the displacement related amount. Therefore, the pressurizing-mechanism-control displacement measuring circuit 31 performs the measurement of the displacement amount as described above based on the pressure detected by the pressure sensor 13.

On the other hand, the measurement of the displacement amount by the elastic-image-generation displacement measuring circuit 33 is performed based on the ultrasound signal generated by the ultrasound transducer 11 in the same manner as that in the foregoing embodiment 1.

Therefore, in the foregoing embodiment 1, there is the circuit part which is made common to the pressurizing-mechanism-control displacement measuring circuit 31 and the elastic-image-generation displacement measuring circuit 33, but in the present embodiment, the pressurizing-mechanism-control displacement measuring circuit 31 and the elastic-image-generation displacement measuring circuit 33 are configured to be separate circuits.

According to the above embodiment 2, substantially the same effects as those in the foregoing embodiment 1 are obtained and since the displacement related amount is the pressure detected by the pressure sensor 13, it is made possible to measure the displacement amount based on the pressure directly measured by contact with the subject.

Besides, although the ultrasound signal generated by the ultrasound transducer 11 is used as the displacement related amount in the embodiment 1, and the pressure detected by the pressure sensor 13 is used as the displacement related amount in the embodiment 2, the pressurizing-mechanism-control displacement measuring circuit 31 may be configured to use both of them so as to more precisely measure the displacement amount.

Further, in the foregoing, the description is mainly given with respect to the ultrasound observation system 1, but the present invention may be directed to a control method for controlling the ultrasound observation system 1 provided with the automatic pressurizing mechanism 12 in the above described manner, a control program for causing a computer to control the ultrasound observation system 1 provided with the automatic pressurizing mechanism 12 in the above described manner, a computer readable recording medium that stores the control program, etc.

In addition, the present invention is not limited to the above-described embodiments just as they are, and can be embodied by modifying the elements within a range not to deviate from the gist of the invention at a stage of carrying out the invention. Further, various aspects of the invention can be formed by appropriate combination of the plurality of elements disclosed in the above embodiments. For example, some elements may be omitted in all the elements shown in the embodiments. Furthermore, the elements in the different embodiments may be combined appropriately. Thus, it is a matter of course that various modifications and applications are possible within the range not to deviate from the gist of the invention.

What is claimed is:

1. An ultrasound observation system for transmitting ultrasound to a subject, receiving the ultrasound reflected by the subject, and generating an image based on an ultrasound signal obtained by the received ultrasound, the ultrasound observation system comprising:

an ultrasound transducer that transmits the ultrasound to the subject, receives the ultrasound reflected by the subject and generates the ultrasound signal from the received ultrasound;

a pressurizing mechanism comprising a pressurizing surface that applies a pressing force to the subject to cause pressurizing displacement;

a displacement-related-amount detector that detects a displacement related amount relating to displacement of the subject;

an elastic-image displacement measuring circuit that measures an imaging displacement amount of the subject based on the ultrasound signal so as to generate an elastic image of the subject;

an elastic modulus calculation circuit that calculates an elastic modulus of the subject based on the imaging displacement amount;

a pressurizing-control displacement measuring circuit that measures a controlling displacement amount in accordance with spontaneous displacement of the subject based on the displacement related amount so as to control the pressurizing mechanism; and a pressurizing mechanism control circuit that controls the pressurizing mechanism based on the controlling displacement amount.

2. The ultrasound observation system according to claim 1, wherein the pressurizing mechanism control circuit estimates the controlling displacement amount on a basis of the pressurizing displacement from timing at which the pressurizing mechanism, applies the pressing force, and calculates a period on a basis of the spontaneous displacement by calculating a period at which the controlling displacement amount is equal to or greater than a preset threshold with the estimated controlling displacement amount excluded.

3. The ultrasound observation system according to claim 2, wherein the pressurizing mechanism control circuit controls the pressurizing mechanism by generating a trigger signal and outputting the trigger signal to the pressurizing mechanism and the pressurizing mechanism applies the pressing force at timing on a basis of the trigger signal.

4. The ultrasound observation system according to claim 3, wherein the pressurizing mechanism control circuit further measures the period by timing when the controlling displacement amount exceeds the threshold.

5. The ultrasound observation system according to claim 4, wherein the pressurizing mechanism control circuit generates the trigger signal such that, when the controlling displacement amount on the basis of the pressurizing displacement is measured by the pressurizing-control displacement measuring circuit, timing when the measured displacement exceeds the threshold occurs at an equally divided point of the period, and outputs the trigger signal to the pressurizing mechanism.

6. The ultrasound observation system according to claim 5, wherein the pressurizing mechanism control circuit further controls the number of trigger signals to be generated within the one period.

7. The ultrasound observation system according to claim 6, wherein the pressurizing mechanism control circuit sets the number of trigger signals to be generated within the one period based on a frame rate of the elastic image.

8. The ultrasound observation system according to claim 1, wherein the pressurizing mechanism control circuit controls the pressurizing mechanism to apply the pressing force to the subject to cause the pressurizing displacement at a fixed period irrespective of the spontaneous displacement, if a time period in which the controlling displacement amount is less than the threshold is equal to or longer than a predetermined time period.

9. The ultrasound observation system according to claim 8, wherein the predetermined time period is an upper-limit time period which is assumable as a period of the spontaneous displacement of the subject.

10. The ultrasound observation system according to claim 9, wherein the upper-limit time period which is assumable as the period of the spontaneous displacement of the subject is an upper-limit time period which is assumable as a beat pulse period of a living body.

11. The ultrasound observation system according to claim 10, wherein the pressurizing mechanism control circuit sets the fixed period based on a frame rate of the elastic image.

12. The ultrasound observation system according to claim 1, wherein the pressurizing mechanism control circuit calculates a maximum value of the controlling displacement amount on the basis of the spontaneous displacement and controls the pressurizing mechanism so that a value equivalent to the calculated maximum value is obtained as a maximum value of the controlling displacement value on the basis of the pressurizing displacement.

13. The ultrasound observation system according to claim 1, wherein the displacement-related-amount detector comprises a pressure sensor and the displacement related amount is a pressure detected by the pressure sensor.

14. The ultrasound observation system according to claim 1, further comprising:
a probe; and
an ultrasound observation apparatus,
wherein the ultrasound transducer, the pressurizing mechanism and the displacement-related-amount detector are provided at the probe, and the elastic-image displacement measuring circuit, the elastic modulus calculation circuit, the pressurizing-control displacement measuring circuit and the pressurizing mechanism control circuit are provided at the ultrasound observation apparatus.

15. The ultrasound observation system according to claim 1, wherein the pressurizing mechanism control circuit calculates a period at which the controlling displacement amount on a basis of the spontaneous displacement of the subject is equal to or greater than a preset threshold, and controls the pressurizing mechanism to apply the pressing force at timing in accordance with the calculated period.

16. A non-transitory computer-readable recording medium storing a program that when executed by a computer causes the computer to perform an operation method of an ultrasound observation system for transmitting ultrasound to a subject, receiving the ultrasound reflected by the subject, and generating an image based on an ultrasound signal obtained by the received ultrasound, the ultrasound observation system comprising:
an ultrasound transducer that transmits the ultrasound to the subject, receives the ultrasound reflected by the subject and generates the ultrasound signal from the received ultrasound;
a pressurizing mechanism comprising a pressurizing surface that applies a pressing force to the subject to cause pressurizing displacement; and
a displacement-related-amount detector that detects a displacement related amount relating to displacement of the subject,
wherein the operation method comprises:
measuring an imaging displacement amount of the subject based on the ultrasound signal so as to generate an elastic image of the subject;
calculating an elastic modulus of the subject based on the imaging displacement amount;
measuring a controlling displacement amount in accordance with spontaneous displacement of the subject based on the displacement related amount so as to control the pressurizing mechanism; and
controlling the pressurizing mechanism based on the controlling displacement amount.

* * * * *

UNITED STATES PATENT AND TRADEMARK OFFICE
CERTIFICATE OF CORRECTION

| | | |
|---|---|---|
| PATENT NO. | : 9,332,964 B2 | |
| APPLICATION NO. | : 14/339006 | |
| DATED | : May 10, 2016 | |
| INVENTOR(S) | : Tatsuya Miyake | |

Page 1 of 1

It is certified that error appears in the above-identified patent and that said Letters Patent is hereby corrected as shown below:

On the title page item (71) should read:

(71)  Applicant:   OLYMPUS CORPORATION., Tokyo (JP)

Signed and Sealed this
Nineteenth Day of July, 2016

Michelle K. Lee
*Director of the United States Patent and Trademark Office*